(12) United States Patent
Kelly et al.

(10) Patent No.: US 6,344,458 B1
(45) Date of Patent: Feb. 5, 2002

(54) PIPERAZINE ETHYLAMIDE DERIVATIVES

(75) Inventors: Michael G. Kelly, Newbury Park, CA (US); Yvette L. Palmer, Yardley, PA (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/459,792

(22) Filed: Dec. 13, 1999

Related U.S. Application Data
(60) Provisional application No. 60/126,448, filed on Dec. 17, 1998.

(51) Int. Cl.⁷ .................... A61K 31/495; A61K 31/496; C07D 295/15
(52) U.S. Cl. ............................ 514/255.03; 514/252.13; 514/252.14; 514/253.01; 514/254.09; 514/254.1; 514/254.11; 544/295; 544/360; 544/364; 544/373; 544/377; 544/379; 544/393
(58) Field of Search .................................. 544/393, 360, 544/364, 295, 373, 377, 379; 514/255.03, 252.13, 252.14, 253.01, 254.09, 254.1, 254.11

(56) References Cited

U.S. PATENT DOCUMENTS

| | | | |
|---|---|---|---|
| 4,988,814 A | 1/1991 | Abou-Gharbia et al. | 544/295 |
| 5,143,916 A | 9/1992 | Lavielle et al. | 514/255 |
| 5,166,157 A | 11/1992 | Lavielle et al. | 514/255 |
| 5,246,935 A | 9/1993 | Jeppessen et al. | 514/253 |
| 5,532,242 A | 7/1996 | Cliffe | 514/255 |
| 5,605,896 A | 2/1997 | Leonardi et al. | 514/218 |
| 5,607,936 A | 3/1997 | Chiang et al. | 514/255 |

FOREIGN PATENT DOCUMENTS

| | | |
|---|---|---|
| EP | 0295010 | 6/1988 |
| EP | 0496692 | 1/1992 |
| EP | 0512755 | 1/1995 |
| GB | 2263110 | 7/1993 |
| WO | WO 9500131 | 1/1995 |
| WO | WO 9920621 | 4/1999 |

OTHER PUBLICATIONS

Saxena, P.R., Pharmac. Ther. vol. 66, 339–368 (1995).

*Primary Examiner*—Emily Bernhardt
(74) *Attorney, Agent, or Firm*—Rebecca R. Barrett

(57) ABSTRACT

Compounds of the formula

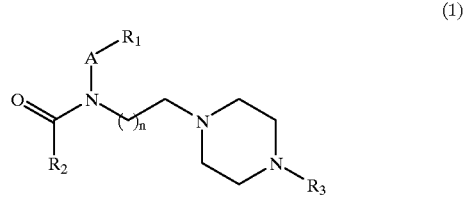

are useful for the treatment of disorder of the central nervous system including anxiety, depression, panic, alcohol and drug addiction, sexual dysfunction, sleep disorders, migraine, obesity, cognitive disorders, and neurodegenerative diseases.

8 Claims, No Drawings

PIPERAZINE ETHYLAMIDE DERIVATIVES

This application claims the benefit of U.S. Provisional Application No. 60/126,448, filed Dec. 17, 1998.

BACKGROUND OF THE INVENTION

U.S. Pat. No. 5,143,916 and divisionals thereof describe (1-naphthyl)-4-alkylpiperazine compounds disclosed as 5-HT1A receptor agonist and antagonist ligands that decrease arterial blood pressure and heart rate.

ES 2027898 describes (2-methoxyphenyl)piperazine derivatives with 5-HT1A receptor activity which are secondary amide and secondary amine derivatives.

SUMMARY OF THE PRESENT INVENTION

In accordance with this invention are provided novel piperazine ethylamide derivatives which are agonists and antagonists of the 5HT1A receptor subtype. By virtue of their high binding affinity to the 5HT1A receptor, compounds of the present invention are useful for the treatment of central nervous system (CNS) disorders such as depression, anxiety, panic, obsessive-compulsive disorder (OCD), sleep disorders, sexual dysfunction, alcohol and drug addiction, cognition enhancement, Alzheimer's disease, Parkinson's disease, obesity and migraine.

Compounds of the present invention are represented by the general formula (1),

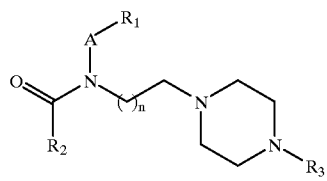

(1)

in which:
R1 is aryl, heteroaryl, cycloalkyl or heterocycloalkyl;
R2 is cycloalkyl, alkyl or $N(R_4R_5)$;
R3 is aryl or heteroaryl;
R4 and R5 are independently hydrogen, alkyl, cycloalkyl, heterocycloalkyl, alkylcycloalkyl, alkylheterocycloalkyl, aryl or heteroaryl, or taken together R4 and
R5 form a heterocycloalkyl; provided that R4 and R5 are not both hydrogen;
A is $(CH_2)m$;
m is an integer from 1 to 4; and
n is an integer from 1 to 3; or a pharmaceutical salt thereof.

In preferred embodiments of the present invention, R1 is aryl, R2 is cycloalkyl and R3 is phenyl.

"Alkyl" as used herein means a branched or straight chain having from 1 to 6 carbon atoms and more preferably 1 to 3 carbon atoms. Exemplary alkyl groups include methyl, ethyl, propyl, isopropyl, butyl, isobutyl, t-butyl, pentyl and hexyl.

"Alkoxy" as used herein means an alkyl-O group in which the alkyl group is as previously described. Exemplary alkoxy groups include methoxy, ethoxy, n-propoxy, i-propoxy, n-butoxy, and t-butoxy.

"Aryl" as used herein means mono or bicyclic aromatic ring having from 6 to 10 carbon atoms. Monocyclic rings preferably have 6 members and bicyclic rings preferably have 8, 9 or 10 membered ring structures. Exemplary aryl groups include phenyl and naphthyl. In some preferred embodiments aryl is phenyl, 1-naphthyl or 2-naphthyl. The aryl group may be substituted with one or more substituents. Substituted aryl groups preferably have one to three substituents.

"Cycloalkyl" as used herein means a monocyclic alkyl group having from 3 to 8 carbon atoms. In some preferred embodiments cycloalkyl may be substituted with from 1 to 3 substituents.

"Heterocycloalkyl" as used herein means a monocyclic alkyl group having from 3 to 8 members including from 1 to 3 heteroatoms selected from N, O and S. In some preferred embodiments heterocycloalkyl may be substituted with 1 to 3 substituents.

Halogen, as used herein means fluorine, chlorine, iodine and bromine.

"Heteroaryl" means 5 to 10 membered mono or bicyclic aromatic ring having from 1 to 3 heteroatoms selected from N, O and S. Monocyclic rings preferably have 5 or 6 members and bicyclic rings preferably have 8, 9 or 10 membered ring structures. Exemplary heteroaryls include pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl and benzodioxanyl. Preferred heteroaryl groups include thienyl, pyridyl, pyrimidinyl, indolyl, and benzodioxanyl. More preferred are heteroaryl groups including 3-thienyl, 2-pyridyl, 2-pyrimidinyl, indol-4-yl and benzodioxan-5-yl. The heteroaryl group may be substituted with one or more substituents. Substituted heteroaryl groups preferably have from 1 to 3 substituents.

Suitable substituents include, unless otherwise noted, halogen, alkyl, hydroxy, alkoxy, amino, amido, nitro, alkylamino, alkylamido, perhaloalkyl, carboxyalkyl, carboxy, carbamide, dialkylamino and aryl.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, alkylcycloalkyl means an alkyl-cycloalkyl group in which alkyl and cycloalkyl are as previously described.

Pharmaceutically acceptable salts are the acid addition salts which can be formed from a compound of the above general formula and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid, and the like.

The compounds of this invention contain a chiral center, providing for various seteroisomeric forms of the compounds such as racemic mixtures as well as the individual optical isomers. The individual isomers can be prepared directly or by asymmetric or stereospecific synthesis or by conventional separation of optical isomers from the racemic mixture.

Compounds of the present invention may be prepared by those skilled in the art of organic synthesis employing conventional methods which utilize readily available reagents and starting materials. For example, reaction of known arylpiperazines (A) with chloroacetonitrile and subsequent reduction with lithium aluminum hydride provides known and novel (4-aryl)piperazine-1-ethylamine derivatives (B). Treatment with acid chlorides provides the subsequent amide (C), which can be reduced to the amine (D)

by the action of a reducing agents such as lithium aluminum hydride or borane. The amine (D) may then be again acylated to provide the required compounds (1) of the present invention.

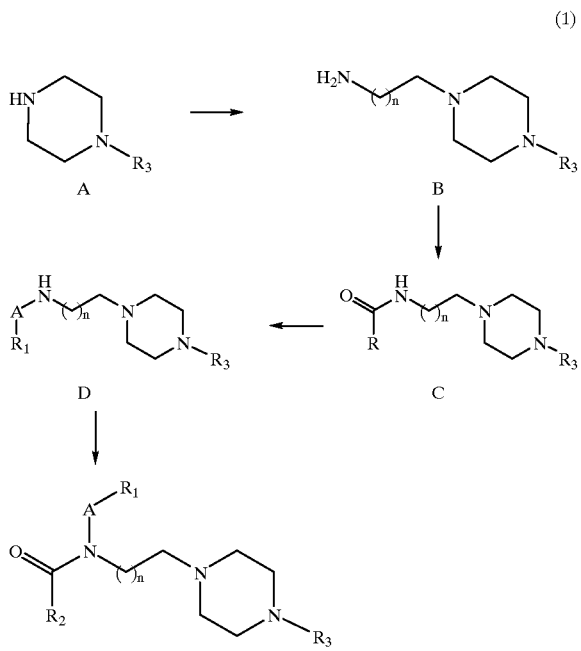

The following non-limiting specific examples are included to illustrate the synthetic procedures used for preparing compounds of formula 1. In these examples, all chemicals and intermediates are either commercially available or can be prepared by standard procedures found in the literature or are known to those skilled in the art of organic synthesis. Several preferred embodiments are described to illustrate the invention. However, it should be understood that the invention is not intended to be limited to the specific embodiments.

COMPOUND 1

N-{2-[4-(2-Methoxy-phenyl)-piperazin-1-yl]-ethyl}-benzamide

Benzoyl chloride (0.30 g, 2.12 mmol) was added dropwise at 0° C. to a solution of 1-(2-aminoethyl)-4-(2-metlhoxyphenyl)piperazine (0.5 g, 2.12 mmol) and triethylamine (2 equivalents, 4.24 mmol) in dichloromethane (20 mL), and the mixture stirred under nitrogen for 16 hours. The solution was evaporated, water (50 mL) added and the product extracted into ethyl acetate (3×25 mL). The combined organics were washed with water (25 mL), brine (25 mL) and dried over anhydrous sodium sulfate. Filtration and concentration in vacuum afforded a white solid (0.66 g, 94% yield). Treatment of the amide with an ethanolic solution of fumaric acid afforded the salt of the titled compound as a white solid.

m.p. 136–138° C. Elemental Analysis for: $C_{20}H_{25}N_3O_2$ $0.5C_4H_4O_4$ $0.75H_2O$; Calculated: C, 64.29; H, 6.99; N, 10.22; Found: C, 64.08; H, 6.88; N, 10.04

COMPOUND 2

Cyclohexanecarboxylic acid benzyl-{2-[4-(2-methoxy-phenyl)-piperazin-1-yl]-ethyl}-amide A solution of the amide (0.279 g, 0.82 mmol) from example 1 in THF (3 mL) was treated with the dropwise addition of 1M $BH_3$—THF (3 mL) and the resulting mixture refluxed under a nitrogen atmosphere for 3 hours. The solution was cooled to 0° C., and the excess borane reagent destroyed by the careful addition of 2N—HCl. After stirring for 2 hours, the solution was made basic with 2N—NaOH and the product extracted with EtOAc (3×25 mL). The combined organics were washed with water (2×20 mL), brine (25 mL) and dried over anhydrous sodium sulfate. Filtration and concentration in vacuum afforded the required amine as a light yellow oil (0.23 g, 88% yield).

Cyclohexanecarbonyl chloride (0.11 g, 0.75 mmol) was added to a $CH_2Cl_2$ solution (10 mL) of the amine 0.23 g , 0.71 mmol) and triethylamine (0.2 mL). After stirring for 16 hours, the solvent was evaporated, water (25 mL) added and the product extracted into EtOAc (3×20 mL). the combined organics were washed with water (20 mL), brine (20 mL) and dried over sodium sulfate. Filtration and concentration gave a viscous yellow oil (0.29 g) which was purified by flash silica gel chromatography to afford the required product (0.24 g, 80% yield). An ethanolic solution of the amide was treated with an ethanolic fumaric acid solution (1 eq) to gave the fumarate salt of the titled compound as a white solid.

m.p. 144–146° C. Elemental Analysis for: $C_{27}H_{37}N_3O_2$ $1.0C_4H_4O_4$; Calculated: C, 67.49; H, 7.49; N, 7.62; Found: C, 67.50; H, 7.49; N, 7.63.

COMPOUND 3

Naphthalene-1-carboxylic acid{2-[4-(2-methoxy-phenyl)-piperazin-1-yl]-ethyl}-amide 1-Naphthoyl chloride (0.40 g, 2.12 mmol) was added dropwise at 0° C. to a solution of 1-(2-aminoethyl)-4-(2-methoxyphenyl)piperazine (0.5 g, 2.12 mmol) and triethylamine (2 equivalents, 4.24 mmol) in dichloromethane (20 (mL), and the mixture stirred under nitrogen for 16 hours. The solution was evaporated, water (50 mL) added and the product extracted into ethyl acetate (3×25 mL). The combined organics were washed with water (25 mL), brine (25 mL) and dried over anhydrous sodium sulfate. Filtration and concentration in vacuum afforded a white solid (0.52 g, 65% yield). Treatment of the amide with an ethanolic solution of flumaric acid afforded the salt of the titled compound as a white solid.

m.p. 136–138° C. Elemental Analysis for: $C_{24}H_{27}N_3O_2$ $0.5C_4H_4O_4$ $0.5H_2O$; Calculated: C, 68.40; H, 6.62; N, 9.20; Found: C, 68.34; H, 6.82; N, 9.08.

COMPOUND 4

Cyclohexanecarboxylic acid{2-[4-(2-methoxy-phenyl)-piperazin-1-yl]-ethyl}-naphthalen-1-ylmethl-amide A solution of the amide (0.473 g, 1.21 mmol) from example 3 in THF (7 mL) was treated with the dropwise addition of 1M $BH_3$—THF (5 mL) and the resulting mixture refluxed under a nitrogen atmosphere for 3 hours. The solution was cooled to 0° C., and the excess borane reagent destroyed by the careful addition of 2N—-HCl. After stirring for 2 hours, the solution was made basic with 2N—NaOH and the product extracted with EtOAc (3×25 mL). The combined organics were washed with water (2×20 mL), brine (25 mL) and dried over anhydrous sodium sulfate. Filtration and concentration in vacuum afforded the required amine as a light yellow oil (0.14 g, 31% yield).

Cyclohexanecarbonyl chloride (0.055 g, 0.37 mmol) was added to a $CH_2Cl_2$ solution (7 mL) of the amine (0.14 g , 0.37 mmol) and triethylamine (0.1mL). After stirring for 16 hours, the solvent was evaporated, water (25 mL) added and the product extracted into EtOAc (3×20 mL). the combined organics were washed with water (20 mL), brine (20 mL) and dried over sodium sulfate. Filtration and concentration gave a viscous yellow oil (0.29 g) which was purified by flash silica gel chromatography to afford the required product (0.1 g, 55% yield). An ethanolic solution of the amide was treated with an ethanolic fumaric acid solution (1 eq) to gave the fumarate salt of the titled compound as a white solid.

m.p. 204–206° C. Elemental Analysis for: $C_{31}H_{39}N_3O_2$ $1.0C_4H_4O_4$; Calculated: C, 69.86; H, 7.20; N, 6.98; Found: C, 69.49; H, 7.21; N, 6.85.

COMPOUND 5

Napthalene-2-carboxylic acid{2-[4-(2-methoxy-phenyl-piperazin-1-yl]-ethyl}-amide 2-Naphthoyl chloride (0.40 g, 2.12 mmol) was added dropwise at 0° C. to a solution of 1-(2-aminoethyl)-4-(2-methoxyphenyl)piperazine (0.5 g, 2.12 mmol) and triethylamine (2 equivalents, 4.24 mmol) in dichloromethane (10 mL,) and the mixture stirred under nitrogen for 16 hours. The solution was evaporated, water (50mL) added and the product extracted into ethyl acetate (3×25 mL). The combined organics were washed with water (25 mL), brine (25 mL) and dried over anhydrous sodium sulfate. Filtration and concentration in vacuum afforded a white solid (0.46 g, 57% yield). Treatment of the amide with an ethanolic solution of fumaric acid afforded the salt of the titled compound as a white solid.

m.p. 136–138° C. Elemental Analysis for: $C_{24}H_{27}N_3O_2$ $0.5C_4H_4O_4$ $1.0H_2O$; Calculated: C, 67.08; H, 6.71; N, 9.03; Found: C, 67.29; H, 6.51; N, 8.92.

COMPOUND 6

Cyclohexanecarboxylic acid-{2-[4-(2-methoxy-phenyl)-piperazin-1-yl]-ethyl}-naphthalen-2-ylmethyl-amide A solution of the amide (0.406 g, 1.04 mmol) from example 5 in THF (6 mL) was treated with the dropwise addition to 1M $BH_3$—THF (4 mL) and the resulting mixture refluxed under a nitrogen atmosphere for 3 hours. The solution was cooled to 0° C. and the excess borane reagent destroyed by the careful addition of 2N—HCl. After stirring for 2 hours, the solution was made basic with 2N—NaOH and the product extracted with EtOAc (3×25 mL). The combined organics were washed with water (2×20 mL), brine (25 mL) and dried over anhydrous sodium sulfate. Filtration and concentration in vacuum afforded the required amine as a light yellow oil (0.32 g , 82% yield).

Cyclohexanecarbonyl chloride (0.125 g, 0.85 mmol) was added to a $CH_2Cl_2$ solution (10 mL) of the amine (0.32 g, 0.85 mmol) and triethylamine (0.25 mL). After stirring for 16 hours, the solvent was evaporated, water (25 mL) added and the product extracted into EtOAc (3×20 mL). the combined organics were washed with water (20 mL), brine (20 mL) and dried over sodium sulfate. Filtration and concentration gave a viscous yellow oil (0.29 g) which was purified by flash silica gel chromatography to afford the required product (0.19 g, 46% yield). An ethanolic solution of the amide was treated with an ethanolic fumaric acid solution (0.5 eq) to gave the fumarate salt of the titled compound as a white solid.

m.p. 141–1430° C. Elemental Analysis for: $C_{31}H_{39}N_3O_2$ $0.5C_4H_4O_4$; Calculated: C, 72.88; H, 7.76; N, 8.04; Found: C, 72.90; H, 7.60; N, 7.73.

COMPOUND 7

N-{2-[4-(2-Methoxy-phenyl)-piperazin- 1-yl]-ethyl}-3-phenyl-propionamide

Hydrocinnamoyl chloride (0.357 g, 2.12 mmol) was added dropwise at 0° C. to a solution of 1-(2-aminoethyl)-4-(2-methoxyphenyl)piperazine (0.5 g, 2.12 mmol) and triethylamine (2 equivalents, 4.24 mmol) in dichloromethane (20 mL), and the mixture stirred under nitrogen for 16 hours. The solution was evaporated, water (50 mL) added and the product extracted into ethyl acetate (3×25 mL). The combined organics were washed with water (25 mL), brine (25 mL) and dried over anhydrous sodium sulfate. Filtration and concentration in vacuum afforded a white solid (0.41 g, 53% yield). Treatment of the amide with an ethanolic solution of fumaric acid afforded the salt of the titled compound as a white solid.

m.p. 107–108° C. Elemental Analysis for: $C_{22}H_{29}N_3O_2$ $0.5C_4H_4O_4$ $1.0H_2O$; Calculated: C, 64.99; H, 7.50; N, 9.47; Found: C, 64.80; H, 7.11; N, 9.22.

COMPOUND 8

Cyclohexanecarboxylic acid-{2-[4-(2-methoxy-phenyl)-piperazin-1-yl]-ethyl}-(3-phenyl-propyl)-amide A solution of the amide (0.36 g, 0.979 mmol) from example 7 in THF (5 mL) was treated with the dropwise addition of 1M $BH_3$—THF (4 mL) and the resulting mixture refluxed under a nitrogen atmosphere for 3 hours. The solution was cooled to 0° C., and the excess borane reagent destroyed by the careful addition of 2N—HCl. After stirring for 2 hours, the solution was made basic with 2N—NaOH and the product extracted with EtOAc (3×25 mL). The combined organics were washed with water (2×20 mL), brine (25 mL) and dried over anhydrous sodium sulfate. Filtration and concentration in vacuum afforded the required amine as a light yellow oil (0.18 g, 52% yield).

Cyclohexanecarbonyl chloride (0.075 g, 0.50 mmol) was added to a $CH_2Cl_2$ solution (7 mL) of the amine (0.18 g, 0.50 mmol) and triethylamine (0.15 mL). After stirring for 16 hours, the solvent was evaporated, water (25 mL) added and the product extracted into EtOAc (3×20 mL). the combined organics were washed with water (20 mL), brine (20 mL) and dried over sodium sulfate. Filtration and concentration gave a viscous yellow oil (0.29 g) which was purified by flash silica gel chromatography to afford the required product (0.15 g, 65% yield). An ethanolic solution of the amide was treated with an ethanolic fumaric acid solution (0.5 eq) to gave the fumarate salt of the titled compound as a pale yellow colored solid.

Elemental Analysis for: $C_{29}H_{41}N_3O_2$ $1.0C_4H_4O_4$; Calculated: C, 69.01; H, 7.67; N, 7.10; Found: C, 69.17; H, 7.86; N, 7.39;

m.p. 103–105° C.

Compounds of the present invention bind with very high affinity to the 5-HT1A receptor and consequently, they are useful for the treatment of primary disorders of the central nervous system such as depression, anxiety and panic, as well as secondary attending problems such as sleep disorders and sexual dysfunction. Compounds of the present invention are also useful for other disorders of the central nervous system including alcohol and drug addiction, obesity and migraine. Cognition enhancement may be achieved by use of compounds of the present invention and neurodegenerative diseases such as Alzheimer's disease and Parkinson's disease may be treated.

5-HT1A Receptor Binding Assay

High affinity for the serotonin 5-HT$_{1A}$ receptor was established by testing a compound's ability to displace [$^3$H] 8-OH-DPAT binding in CHO cells stably transfected with the human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 µL. Non-specific binding is determined in the presence of 10 mM 5-HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

5-HT1A Receptor Intrinsic Activity Assay

The intrinsic activity of compounds of the present invention was established by testing the claimed compounds ability to reverse the stimulation of cyclic adenosinemonophosphate (cAMP) in CHO cells stably transfected with the human 5-HT1A receptor.

Stably transfected CHO cells were grown in DMEM containing 10% heat inactivated FBS and non-essential amino acids. The cells are plated at a density of x10$^6$ cells per well in a 24 well plate and incubated for 2 days in a CO$_2$ incubator. On the second day, the media is replaced with 0.5 mL treatment buffer (DMEM+25 mM HEPES, 5 mM theophylline, 10 µM pargyline) and incubated for 10 minutes at 37° C. Wells are treated with forskolin (1 µM final concentration) followed immediately by the test compound (0.1 and 1 µM for initial screen) and incubated for an additional 10 minutes at 37° C. The reaction is terminated by removal of the media and addition of 0.5 mL ice cold assay buffer (supplied in the RIA kit). Plates are stored at −20° C. prior to assessment of cAMP formation by RIA. EC$_{50}$ values are determined for the active test compounds. Compounds shown to have no agonist activities (Emax=0%) are further analyzed for their ability to reverse agonist induced activity. In separate experiments, 6 concentrations of antagonist are preincubated for 20 minutes prior to the addition of agonist and forskolin. Cells are harvested as described above. The cAMP kit is supplied by Amersham and the RIA is performed as per kit instructions, and calculations of IC$_{50}$ performed by GraphPad Prism.

|  | 5-HT1A binding | | |
| --- | --- | --- | --- |
| Compound | Ki (nM) | Emax | cAMP |
| Compound 2 | 1.8 | 36% | (EC$_{50}$ = 4.2 nM) |
| Compound 4 | 26 | 88% | |
| Compound 6 | 1.2 | 0% | (IC$_{50}$ = 24 nM) |
| Compound 8 | 20 | 77% | |

Hence, compounds of the present invention exhibit high affinity for the 5HT1A receptor subtype and exhibit intrinsic activity as evidenced by their ability to reverse stimulation of cyclic adenosinemonophosphate (cAMP). Accordingly, compounds of the present invention are useful for treatment of disorders of the central nervous system and may be administered to a patient suffering from one or more of said disorders. Treatment, as used herein, refers to alleviation or amelioration of symptoms of a particular disorder in a patient. In addition, compounds of the present invention may be administered as part of a treatment regime that includes other agents which act on the central nervous system. In some preferred embodiments, compounds of the present invention are part of a combination therapy including a serotonin reuptake inhibitor. Serotonin reuptake inhibitors useful in combination therapies of the present invention fluoxetine, fluvoxamine, paroxetine, sertraline and venlafaxine. Said agents may be administered at the same time, where they may be combined into a single dosage form, or at a different time, as compounds of the present invention, while still being part of the regime of the combination therapy.

Compounds of the invention may be administered to a patient either neat or with a convention pharmaceutical carrier.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils of fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. The novel method of the invention for treating conditions related to or are affected by the 5-HT1A receptor comprise administering to warm-blooded animals, including humans, an effective amount of at least one compound of Formula 1 and its non-toxic, pharmaceutically acceptable addition salts. The compounds may be administered orally, rectally, parenterally or topically to the skin and mucosa. The usual daily dose is depending on the specific compound, method of treatment and condition treated. The usual daily dose is 0.01–1000 mg/Kg for oral application, preferably 0.5–500 mg/Kg, and 0.1–100mg/Kg for parenteral application, preferably 0.5–50 mg/Kg.

What is claimed is:

1. A compound of Formula (1),

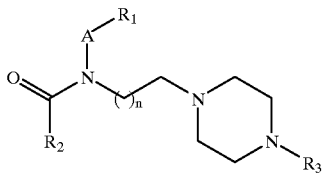

(1)

in which:
R1 is naphthyl, 2-pyridyl, 2-pyrimidyl, benzodioxan-5-yl, indol-4-yl, 3-thienyl, or cycloalkyl;
R2 is cycloalkyl or alkyl;
R3 is aryl, 2-pyridyl, 2-pyrimidyl, benzodioxan-5-yl, indol-4-yl or 3-thienyl;
A is (CH$_2$)m;
m is an integer from 1 to 4; and
n is an integer from 1 to 3; or a pharmaceutical salt thereof.

2. A compound which is cyclohexanecarboxylic acid{2-[4-(2-methoxy-phenyl)-piperazin-1-yl]-ethyl}-naphthalen-1-ylmethyl-amide; or a pharmaceutically acceptable salt thereof.

3. A compound which is cyclohexanecarboxylic acid-{2-[4-(2-methoxy-phenyl)-piperazin-1-yl]-ethyl}-naphthalen-2-ylmethyl-amide; or a pharmaceutically acceptable salt thereof.

4. A compound which is Cyclohexanecarboxylic acid-{2-[4-(2-methoxy-phenyl)-piperazin-1-yl]-ethyl}-(3-phenyl-propyl)-amide; or a pharmaceutically acceptable salt thereof.

5. A pharmaceutical composition comprising a compound of claim 1 and a pharmaceutically acceptable carrier.

6. A method of treating a patient suffering from a disorder of the central nervous system associated with the 5-hydroxytryptamine-1A receptor subtype selected from the group consisting of depression, anxiety, and panic comprising administering a therapeutically effective amount of a compound of Formula (1),

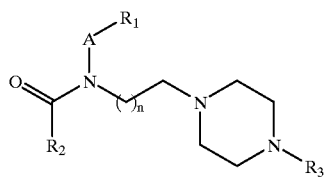

(1)

in which:
R1 is naphthyl, 2-pyridyl, 2-pyrimidyl, benzodioxan-5-yl, indol-4-yl, 3-thienyl, or cycloalkyl;
R2 is cycloalkyl or alkyl;
R3 is aryl, 2-pyridyl, 2-pyrimidyl, benzodioxan-5-yl, indol-4-yl or 3-thienyl;
A is (CH$_2$)m;
m is an integer from 1 to 4; and
n is an integer from 1 to 3; or a pharmaceutical salt thereof.

7. A method of treating a patient suffering depression, anxiety or panic comprising administering a therapeutically effective amount of a compound which is
cyclohexanecarboxylic acid{2-[4-(2-methoxy-phenyl)-piperazin-1-yl]-ethyl}-naphthalen-1-ylmethyl-amide;
cyclohexanecarboxylic acid-{2-[4-(2-methoxy-phenyl)-piperazin-1-yl]-ethyl}-naphthalen-2-ylmethyl-amide; or
cyclohexanecarboxylic acid-{2-[4-(2-methoxy-phenyl)-piperazin-1-yl]-ethyl}-(3-phenyl-propyl)-amide; or pharmaceutically acceptable salts thereof.

8. A pharmaceutical composition comprising
cyclohexanecarboxylic acid{2-[4-(2-methoxy-phenyl)-piperazin-1-yl]-ethyl}-naphthalen-1-ylmethyl-amide;
cyclohexanecarboxylic acid-{2-[4-(2-methoxy-phenyl)-piperazin-1-yl]-ethyl}-naphthalen-2-ylmethyl-amide; or
cyclohexanecarboxylic acid-{2-[4-(2-methoxy-phenyl)-piperazin-1-yl]-ethyl}-(3-phenyl-propyl)-amide; or pharmaceutically acceptable salts thereof; and a pharmaceutically acceptable carrier.

* * * * *